United States Patent [19]

Fischer et al.

[11] Patent Number: 4,927,603
[45] Date of Patent: May 22, 1990

[54] FEEDING DEVICE FOR INTRODUCING LIQUID OR GASEOUS SAMPLES

[75] Inventors: Fritz Fischer; Erich Kleinhappl; Hermann Marsoner, all of Graz, Austria

[73] Assignee: AVL AG, Switzerland

[21] Appl. No.: 213,155

[22] Filed: Jun. 29, 1988

[30] Foreign Application Priority Data

Jul. 2, 1987 [AT] Austria .................................. 1672/87

[51] Int. Cl.$^5$ ............................................. G01N 35/00
[52] U.S. Cl. ........................................ 422/67; 422/63; 422/100; 73/863.01; 73/864.21; 73/864.25
[58] Field of Search .................... 422/63–68, 422/81, 83, 100, 102, 104, 50; 222/526, 533; 141/130, 270, 279, 284, 363; 73/864.21, 864.24, 864.25, 864.31, 864.73, 864.74, 863.01

[56] References Cited

U.S. PATENT DOCUMENTS

| | | | |
|---|---|---|---|
| 3,687,632 | 8/1972 | Natelson | 141/130 |
| 4,113,436 | 9/1978 | Werder et al. | 422/65 |
| 4,499,053 | 2/1985 | Jones | 422/68 |
| 4,570,495 | 2/1986 | Terada | 73/864.25 |
| 4,705,667 | 11/1987 | Marsoner et al. | 422/68 |
| 4,720,463 | 1/1988 | Farber et al. | 435/291 |

FOREIGN PATENT DOCUMENTS

| | | |
|---|---|---|
| 381794 | 11/1986 | Austria . |
| 1169614 | 11/1969 | United Kingdom . |
| 1497012 | 1/1978 | United Kingdom . |

Primary Examiner—Robert J. Warden
Assistant Examiner—D. John Griffith, Jr.
Attorney, Agent, or Firm—Watson, Cole, Grindle & Watson

[57] ABSTRACT

A feeding device for introducing liquid or gaseous media into the analysis path of an analyzing apparatus includes a feeder element which cooperates in an initial position with a feed opening for calibrating or cleansing media and which may by brought into one or more sample feed positions. The feeder element is fastened by means of chain pins to a driven link chain which is guided by a guide pulley, the chain permitting the feeder element to be moved from the initial position and then tilted into a sample feed position upon contact of the feeder element with the guide pulley.

7 Claims, 3 Drawing Sheets

FEEDING DEVICE FOR INTRODUCING LIQUID OR GASEOUS SAMPLES

BACKGROUND OF THE INVENTION

This invention relates to a feeding device for introducing liquid or gaseous media into the analysis path of an analyzing apparatus, comprising a feeder element preferably provided with a hollow needle, which, in its initial position, cooperates with a feed opening for calibrating or cleansing media, and which may be brought into one or mroe sample feed positions.

DESCRIPTION OF THE PRIOR ART

A feeding device of the above kind is described in Austrian Pat. No. 381,794. In this patent the feeding device comprises a feeder element which may be tilted from an initial position into a sample feed position, and is configured as a hollow needle to be positioned by a lever mechanism, which needle cooperates with a funnel-shaped feed opening in its initial position. Since a reference or cleansing media, as well as a quantity of air that may be required for drying the sample path, may enter through the feed opening into the feeder element in the initial position, a very simple configuration of hte analyzing apparatus is achieved where no valves or other shut-off devices are required in the path of analysis to be travelled by the sample once it has passed the feed opening. Only for sample intake must the sealing contact between feeder element and funnel-shaped feed opening be broken and the feeder element tilted into the intake position for picking up the sample; in all other operational states of the analyzing apparatus the media path between the individual feeder vessels and the waste vessel is fixed and closed, the medium actually entering into the path of analysis being controlled via three valves only.

The only disadvantage of the above feeding device is the relatively complicated mechanism of levers moving the feeder element from initial to feed position. With this mechanism, the feeder element must be lifted from the funnel-shaped feed opening in a direction parallel to the axis of this opening, before it is tilted into the sample feed position. The necessary lifting/tilting movement is achieved by the combined action of a tilting arm and a tilting lever which are set in motion by an actuating flap on the housing of the apparatus.

In British Pat. No. 1,169,614 a sampling device is disclosed which is provided with a hollow needle that is lifted and lowered by a belt running on a guide pulley. In this known device the hollow needle can only be lifted and lowered, however. This results in a relatively complicated process of sample feeding.

SUMMARY OF THE INVENTION

It is an object of the invention to propose a mechanism based on the known feeding device referred to above, which will permit the sequence of motions necessary for actuating the feeder element to be realized in an uncomplicated design.

In the invention this object is achieved by fastening the feeder element by means of chain pins onto a driven link chain guided by a guide pulley, which chain is used to lift the feeder element from its initial position, in a direction parallel to the axis of the feed opening, and by tilting the feeder element into a sample feed position upon contact with the guide pulley.

The movement of the feeder element, which in the beginning of its motion sequence is parallel to the axis of the feed opening, is achieved by suitably fastening the feeder element to the link chain, i.e., at a point well below the upper guide pulley in the initial position of the device, in order to make sure that the feeder element is pulled out entirely from the respective sample vessel, or rather, from the feed opening of this vessel. Due to these measures a very simple and safe assembly is obtained.

In an enhanced embodiment of the invention the feeder element can be brought into at least one sample intake position cooperating with a sample exchanger during its movement parallel to the axis of the feed opening. This variant of the feeding device thus gives three positions of the feeder element, which is configured, for example, as a hollow needle attached to the driven link chain by means of a needle holder. In the initial position in which the feeder element is cooperating with a feed opening (preferably funnel shaped), cleansing and calibrating media are passed through by means of the pump of the analyzing apparatus, or rather, the feeding device. After a vertical movement of the hollow needle a mean position is reached in which fed samples are automatically picked up from a sample exchanger, the feeder element dipping into the sample vessle by a reverse vertical movement after the arrival of each sample vessel from the sample exchanger. Finally, as the guide pulley moves on, the feeder element will enter a third or top position, in which the hollow needle is tilted in order to introduce single samples. It will be possible, of course, to provide further sample feed or intake positions both in the range of the vertical movement and in that of the tilting movement of the feeder element.

In a particularly advantageous variant of the invention the guide pulley is driven by a stepping motor. The chain, for instance a plastic chain, can be guided in addition to the guide pulley and the pulley of the chain-tightener, by another gear directly driven from the stepping motor. The chain-tightener will stabilize the feeder element in its individual positions.

In the invention the accuracy of the guide elements of the feeder element is further improved between the initial position and the individual feed positions by guiding the ends of the chain pins carrying the feeder element in a slotted part of the housing for additional stabilization of the feeder element, for instance by providing a groove on either side of the chain, in which the ends of the chain pins will slide.

In a further development of the invention a position control element is provided for monitoring the position of the feeder element, with Hall sensors attached on the housing of the device which will cooperate with a magnet located on the feeder element, preferably on the needle holder of the hollow needle. Basically, other kinds of position monitoring devices are conceivable, for example, electro-optical devices; however, Hall sensors are preferred as they are dirt-resistant.

Finally, the invention proposes the use of an electronic control and monitoring unit for control of the stepping motor and for processing of the signals from the position control element, which will result in an automated process of sample feeding operation being restricted to the input of YES-NO decisions via a key panel.

DESCRIPTION OF THE DRAWINGS

Following is a more detailed description of the invention as illustrated by the accompanying drawings, in which.

DETAILED DISCRIPTION OF THE PREFERRED EMBODIMENT

Figure 1:
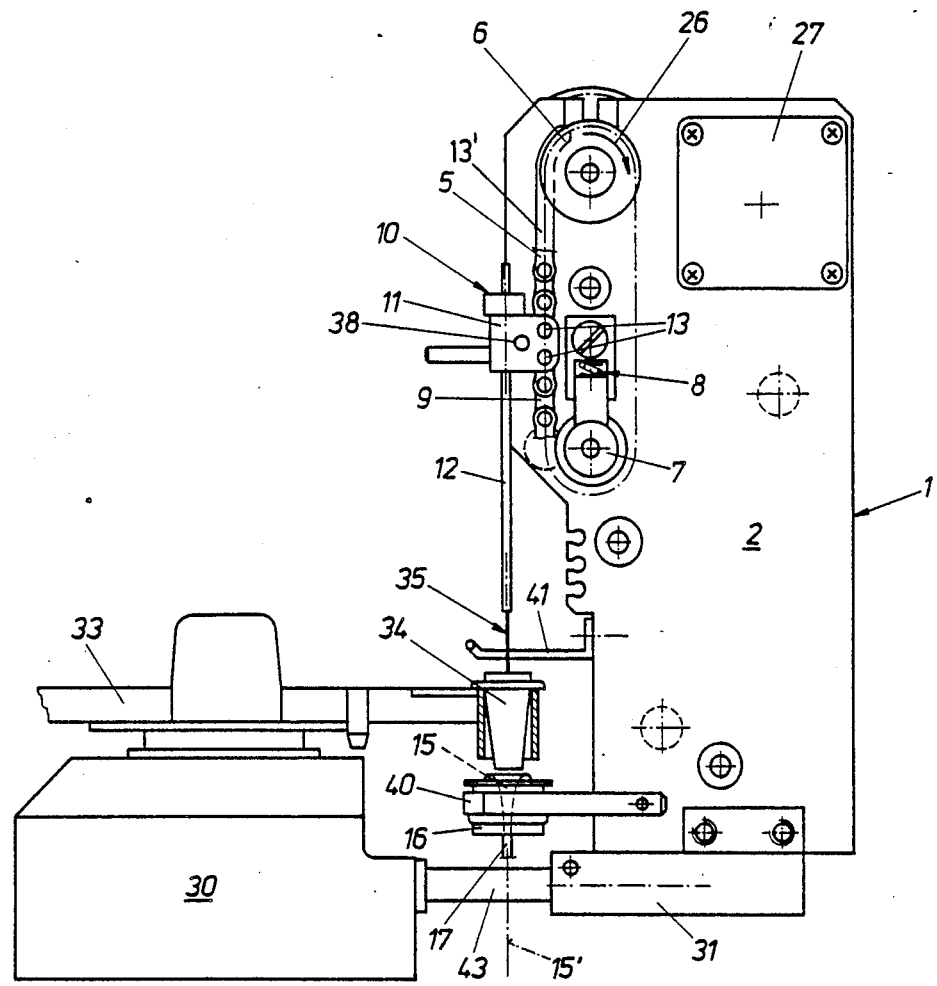
FIGS. 1 and 2 present side views, and FIG. 3 a front view of a feeding device according to the invention.
Figure 2:
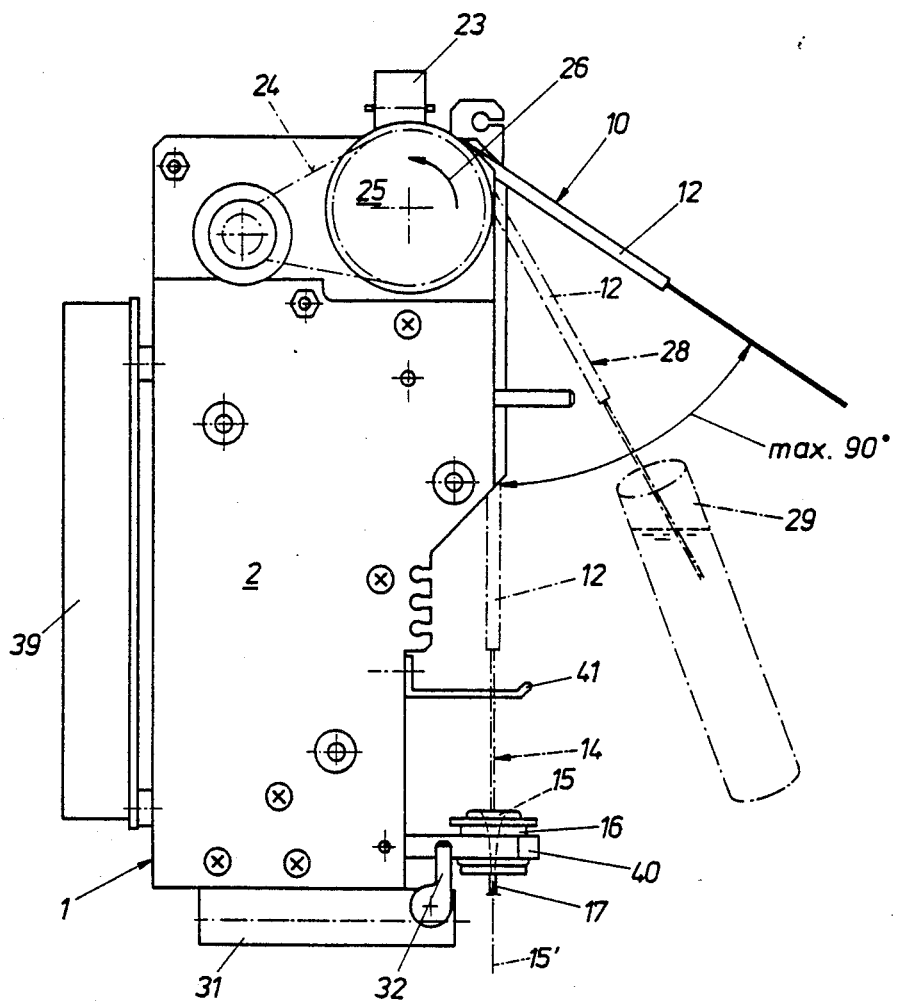
Figure 3:
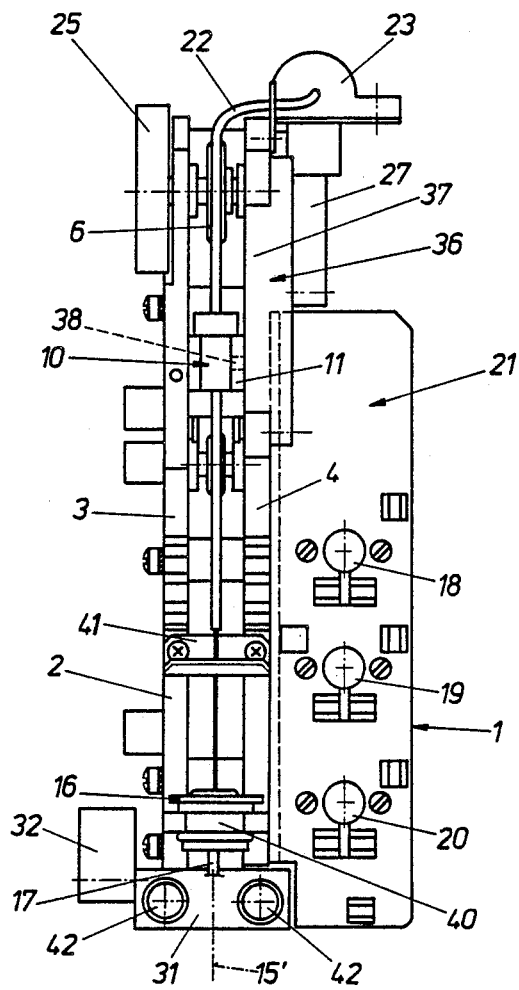

The variant of the feeding device 1 shown in FIGS. 1 to 3 has a housing 2, essentially consisting of parts 3 and 4, between which moves a driven belt 5 guided by the guide pulley 6 and the pulley 7 of the chain tightener 8. The belt 5, which can be driven via the guide pulley 6, is configured as a chain 9 to which is attached the feeder element 10 comprising a needle holder 11 and a hollow needle 12 which is screw-fastened onto the holder. The needle holder 11 is fastened to the chain 9 by means of chain pins 13 guided in a slotted part of the housing 2, for instance by grooves 13 in parts 3 and 4 of the housing 2.

In the initial position 14 the hollow needle 12 of the feeder element 10 is in sealing contact with the feed opening 15 of a funnel element 16 on whose side opposite of the feed opening 15 a calibrating and cleansing media are entered through the feed pipe 17 in a manner already described in Austrian Pat. No. 381,794, via valves 18, 19, 20 of the valve unit 21. The hollow needle 12 is connected to a flexible tube 22 leading to the analysis path of an analyzing apparatus (not shown here) via an optical liquid sensor 23.

The chain 9, which is driven by a stepping motor 27 via a belt 24 and a pulley 25 in the direction of the arrow 26, will lift the hollow needle 12 of the feeder element 10 from the initial position 14, at first parallel to the axis 15' of the feed opening 15, subsequent to which the needle holder 11 will eventually reach the guide pulley 6 by which it is moved through a sector of a circular path, such that the hollow needle is tilted out of the housing 2 into a sample feed position 28. The tilting range limited by a stop is 90° in this instance. In the sample feed position 28 the feeder element 10 may be fed with single samples from any kind of feeder vessel 29.

An automatic sample exchanger 30—shown in FIG. 1—may be centered and fixed in position by means of a coupling 31 with a stop lever 32 via bolts 43 of the sample exchanger 30 that are inserted into bores 42 of the housing 2 of the feeding device. The sample plate 33 of the sample exchanger 30, which carries vessels 34 containing the test samples along its circumference, extends into the path of the hollow needle 12 in the area between the funnel element 16, or rather, its support 40, and a needle protector 41 located on the housing, such that the hollow needle 12 can be dipped into the individual vessles 34 for sample intake, parallel to the axis 15' of the feed opening 15. During this process the feeder element is in the sample intake position 35.

The feeding device 1 is further provided with a position control element 36 comprising Hall sensors 37 located on the housing 2, which sensors cooperate with a magnet 38 on the feeder element 10, for instance on the needle holder 11 of the hollow needle 12. A device for monitoring the position of the feeder element 10 could also be positioned on the chain 9 or the guide pulley 6, of course. In addition, an electronic control and monitoring unit 39 is provided for control of the stepping motor 27 and processing of the signalsfrom the position control element 36.

We claim:

1. A feeding device for introducing liquid or gaseous samples into an analysis path of an analyzing apparatus which comprises
   a link chain mounted on a guide pulley,
   a stepping motor for driving said link chain,
   a control means for controlling the operation of said stepping motor,
   a feeder element comprising a needle holder and a hollow needle, said feeder element being connected to said link chain by chain pins, said control means controlling the operation of said stepping motor and thus the movement of said link chain such that, starting from an initial position where said needle holder is remote from said guide pulley and said hollow needle is located in a feed opening of an element wherein it can be contacted with calibrating or cleansing media, movement of said link chain in a first direction will cause said needle holder to move along an axis defined by the feed opening and, as said needle holder moves around said guide pulley, to tilt said hollow needle relative to said axis into a first sample intake position.

2. A feeding device according to claim 1, comprising a sample exchanger for moving sample vessels into alignment with said axis so that movement of said link chain in a second direction opposite to said first direction will cause said hollow needle to become respectively positioned in a second sample intake position within said sample vessels.

3. A feeding device according to claim 1, wherein said stepping motor is connected to rotate said guide pulley.

4. A feeding device according to claim 1, including slotted means in which ends of said chain pins are guided for stabilizing movement of said feeder element when said link chain is moved in said first and second directions.

5. A feeding device according to claim 4, including first and second housing parts which respectively provide said slotted means.

6. A feeding device according to claim 1, wherein said needle holder includes a magnet and including Hall sensors for detecting the positioning of said magnet, said magnet and Hall sensors constituting a position control device.

7. A feeding device according to claim 6, including a monitoring unit for processing signals from said position control device.

* * * * *

UNITED STATES PATENT AND TRADEMARK OFFICE
CERTIFICATE OF CORRECTION

PATENT NO. : 4,927,603
DATED : May 22, 1990
INVENTOR(S) : Fritz FISCHER et al.

It is certified that error appears in the above-identified patent and that said Letters Patent is hereby corrected as shown below:

On the title page, correct item [73] to read
--[73] Assignee: AVL AG, Schaffhausen, Switzerland--.

Signed and Sealed this

Seventeenth Day of September, 1991

Attest:

HARRY F. MANBECK, JR.

Attesting Officer

Commissioner of Patents and Trademarks